United States Patent
Cavitt et al.

(10) Patent No.: US 9,591,848 B2
(45) Date of Patent: Mar. 14, 2017

(54) BIOFILM RESISTANT POLYMER MATERIALS

(75) Inventors: T. Brian Cavitt, Abilene, TX (US); Rebecca Ann Herrington Faulkner, Abilene, TX (US)

(73) Assignee: Abilene Christian Univ., Abilene, TX (US)

( * ) Notice: Subject to any disclaimer, the term of this patent is extended or adjusted under 35 U.S.C. 154(b) by 394 days.

(21) Appl. No.: 13/115,943

(22) Filed: May 25, 2011

(65) Prior Publication Data

US 2012/0208916 A1 Aug. 16, 2012

Related U.S. Application Data

(62) Division of application No. 12/134,353, filed on Jun. 6, 2008.

(51) Int. Cl.
| | | |
|---|---|---|
| *A01N 25/00* | (2006.01) | |
| *A01N 37/10* | (2006.01) | |
| *C09D 5/14* | (2006.01) | |
| *A61K 6/08* | (2006.01) | |

(52) U.S. Cl.
CPC ............. *A01N 25/00* (2013.01); *A01N 37/10* (2013.01); *C09D 5/14* (2013.01); *A61K 6/08* (2013.01)

(58) Field of Classification Search
None
See application file for complete search history.

(56) References Cited

U.S. PATENT DOCUMENTS

| | | | | |
|---|---|---|---|---|
| 4,555,372 A | * | 11/1985 | Kunzler et al. | 264/2.1 |
| 5,321,889 A | * | 6/1994 | Watanabe | 29/895.3 |
| 5,759,455 A | * | 6/1998 | Kamitakahara et al. | 264/1.34 |
| 6,368,523 B1 | * | 4/2002 | Buazza et al. | 264/1.36 |
| 2009/0087753 A1 | * | 4/2009 | Satou et al. | 430/2 |

FOREIGN PATENT DOCUMENTS

| | | | |
|---|---|---|---|
| EP | 0441383 B1 | * | 2/1991 |
| WO | WO 2007007436 A1 | * | 1/2007 |

* cited by examiner

*Primary Examiner* — Michael G Hartley
*Assistant Examiner* — Lance Rider
(74) *Attorney, Agent, or Firm* — Megan Lyman

(57) ABSTRACT

The present invention relates to compounds and materials that reduce the accumulation of microorganisms on a surface by interfering with the attachment of the organisms to the surface. The compounds and materials of the present invention are thus useful in preventing the formation of biofilms. The compounds of the present invention may be either adhered to a surface or integrated within a polymer. Surfaces coated by the present invention are resistant to biofilm formation, in part due to the smoothness of the surface coated with the present invention.

15 Claims, 4 Drawing Sheets

A) Uncoated, cold-rolled, polished steel.

B) Cold-rolled, polished steel coated with a cured 20% by weight PA formulation.

$S_y = 0.819$ μm $S_y = 5.1233$ μm

C) Cold-rolled, polished steel coated with a cured 20% by weight CPA formulation.

D) Cold-rolled, polished steel coated with a cured 20% by weight DCPA formulation.

| Monomer | 0 wt % | 5 wt % | 10 wt % | 15 wt % | 20 wt % |
|---|---|---|---|---|---|
| PA | 1 | 0 | 0 | 0 | 0 |
| CPA | 1 | 4 | 5 | 5 | 5 |
| DCPA | 1 | 4 | 5 | 5 | 5 |
| BPA | 1 | 3 | 4 | 4 | 4 |
| DBPA | 1 | 3 | 5 | 5 | 5 |

Scale: least 0  1  2  3  4  5 most biofilm resistance

BIOFILM RESISTANT POLYMER MATERIALS

This application is a divisional application, claiming the benefit of U.S. patent application Ser. No. 12/134,353 filed Jun. 6, 2008.

FIELD OF INVENTION

This invention relates to compounds, compositions, and methods for controlling biofilms, i.e., preventing biofilm formation.

BACKGROUND OF TEE INVENTION

Biofilms are mucilaginous communities of microorganisms such as bacteria, archaea, fungi, molds, algae or protozoa or mixtures thereof that grow on various surfaces (see Nature, vol. 408, pp. 284 286, Nov. 16, 2000). Biofilms form when microorganisms establish themselves on a surface and activate genes involved in producing a matrix that includes polysaccharides. The compositions of the present invention may prevent or retard biofilm formation by interfering with a microorganism's ability to attach to a surface.

Molecules called quorum-sensing signals help trigger and coordinate part of the process of forming a biofilm after the microorganism attaches to the surface. Bacteria constantly secrete low levels of the signals and sense them either through receptors on their surfaces, or internally. The receptors trigger behavioral changes when there are enough bacteria to allow the signals' concentrations to achieve a critical threshold. Once this occurs, bacteria respond by adopting communal behavior, such as forming a biofilm, and in the case of pathogenic bacteria, deploying virulence factors such as toxins. In addition to communicating with members of their own species, bacteria also conduct inter-species communications, such that a biofilm may contain more than one species of bacteria.

Biofilms develop preferentially on inert surfaces including those of everyday and household items. Biofilms may form on polymeric materials (e.g., thermoplastic and thermoset), woods, metals, glass and ceramics found in the home and in public areas. For example, biofilm formation is commonplace on sinks and countertops. Exposure to such microorganisms through skin-surface contact may result in infections that compromise the health of the public. In addition to sinks and countertops, biofilms may form on any number of items with which persons come into contact such as: floors, walls, shopping carts, toys, furniture, shelving, hygiene products, playground equipment, and so forth. Controlling formation of biofilms in these areas could result in less infection of individuals in the home and in public.

Biofilm formation has important public health implications as well. Drinking water systems are known to harbor biofilms, even though these environments often contain disinfectants. Any system providing an interface between a surface and a fluid has the potential for biofilm development. Water cooling towers for air conditioners are well-known to pose public health risks from biofilm formation, as episodic outbreaks of infections like Legionnaires' Disease attest. Turbulent fluid flow over the surface does not provide protection; biofilms can form in conduits where flowing water or other fluids pass, with the effects of altering flow characteristics and passing planktonic organisms downstream. Industrial fluid processing operations have experienced mechanical blockages, impedance of heat transfer processes, and biodeterioration of fluid-based industrial products, all attributable to biofilms. Biofilms have been identified in flow conduits like hemodialysis tubing, and in water distribution conduits. Biofilms have also been identified to cause biofouling in selected municipal water storage tanks, private wells and drip irrigation systems, unaffected by treatments with up to 200 ppm chlorine.

Biofilms are a constant problem in food processing environments. Food processing involves fluids, solid material and their combination. As an example, milk processing facilities provide fluid conduits and areas of fluid residence on surfaces. Cleansing milking and milk processing equipment presently utilizes interactions of mechanical, thermal and chemical processes in air-injected clean-in-place methods. Additionally, the milk product itself is treated with pasteurization. In cheese production, biofilms can lead to the production of calcium lactate crystals in cheddar cheese. Meat processing and packing facilities are in like manner susceptible to biofilm formation. Non-metallic and metallic surfaces can be affected. Biofilms in meat processing facilities have been detected on rubber "fingers," plastic curtains, conveyor belt material, evisceration equipment and stainless steel surfaces. Controlling biofilms and microorganism contamination in food processing is hampered by the additional need that the agent used not affect the taste, texture or aesthetics of the product.

Microbial infection, and the subsequent formation of biofilms remains one of the most serious complications in several areas, particularly in medical devices, drugs, health care and hygienic applications, water purification systems, hospital and dental surgery equipment, textiles, food packaging and food storage (See Biomacromolecules, vol. 8 no. 5, pp. 1359-1384, May 2007). Since the difficulties associated with eliminating biofilm-based infections are well-recognized, a number of technologies have developed to treat surfaces or fluids bathing surfaces to prevent or impair biofilm formation. Biofilms adversely affect medical systems and other systems essential to public health such as water supplies and food production facilities. A number of technologies have been proposed that treat surfaces with organic or inorganic materials to interfere with biofilm development. For example, various methods have been employed to coat the surfaces of medical devices with antibiotics (See e.g. U.S. Pat. Nos. 4,107,121, 4,442,133, 4,895,566, 4,917,686, 5,013,306, 4,952,419, 5,853,745 and 5,902,283) and other bacteriostatic compounds (See e.g U.S. Pat. Nos. 4,605,564, 4,886,505, 5,019,096, 5,295,979, 5,328,954, 5,681,575, 5,753,251, 5,770,255, and 5,877, 243). Additionally, significant advances in the last three decades have been made in the synthesis and application of polymers to prevent microbial attack and degradation in many contexts. (See Biotechnol. Bioact. Polym., pp. 225-237, 1994). Despite these advances, contamination of medical devices and invasive infection therefrom continues to be a problem.

Any agent used to impair biofilm formation that will be exposed to individuals must be safe to the user. Certain biocidal agents, in quantities sufficient to interfere with biofilms, also can damage host tissues. Thus, it is advantageous for the biofilm resistant compound to function not as a biocide, but to render surfaces unsuitable for adhesion and colonization by microorganisms. Such a compound relies not on a "kill mechanism" for the prevention of biofilms, but on creating an environment not conducive to biofilm formation.

Until now, it has been postulated that smoother surfaces may delay the initial build up of microorganisms on a surface during biofilm formation, but will not significantly affect the amount of biofilm that will attach to the surface. (See "*The key to understanding and controlling bacterial growth in Automated Drinking Water Systems, Second Edition*" by Edstrom Indus., Inc., pg. 7, June 2003). The present invention demonstrate that biofilm formation may be prevented by coating a surface with the present invention or by incorporating the present invention into the substrate as a whole. The mechanism by which the present invention retards the formation and growth of biofilms is by creating a surface wherein microorganisms associated with biofilms do not adhere or colonize, in part due to the smoothness of the surface coated, or integrated, with the compositions and compounds of the present invention.

BRIEF SUMMARY OF THE INVENTION

The present invention relates to compounds and materials that reduce the accumulation of microorganisms on a surface by interfering with the attachment of the organisms to the surface. The compounds and materials of the present invention are thus useful in preventing the formation of biofilms. The compounds of the present invention may be either adhered to a surface or integrated within a polymer. "Preventing" a biofilm means rendering a surface unsuitable for colonization and growth by microorganisms that form biofilms. Surfaces coated by the present invention are resistant to biofilm formation, in part due to the smoothness of the surface coated with the present invention.

All documents cited are, in relevant part, incorporated herein by reference; the citation of any document is not to be construed as an admission that it is prior art with response to the present invention.

In one aspect, the present invention is a polymerizable (i.e., curable) monomeric composition, having the general Structure A. Structure A may be polymerized onto (e.g., coating) or into (e.g., as a comonomer in a thermoplastic or thermoset polymer matrix) a contact substrate, which may include household items, public use items, medical devices, and other products:

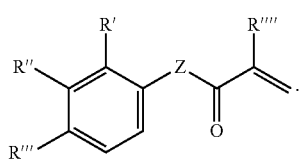

Structure A

In Structure A, R', R", or R'" represents a halogen (e.g., Chlorine or Bromine), Hydrogen, or other organic moiety (e.g., alkyl, aryl, etheric, esteric, amido, amino, thiyl, or other hydrocarbon- or heteronuclear-based functional group) as long as at least one substituent (R', R", R'") is a halogen, R"" represents either a Hydrogen or a Methyl (e.g., $CH_3$) group, and Z represents an Oxygen or other organic moiety as previously defined where one Oxygen binds the organic moiety to the aryl group and another Oxygen binds the organic moiety to the carbonyl adjacent to the depicted alkene. Furthermore, the monomer may be mono- or multi-functional in the number of polymerizable groups (e.g., acrylic or methacrylic groups). The active component of the monomer is its phenyl ring with halogens. The monomer can be covalently bonded to any polymerizable functional group with or without a spacer group (i.e., other atoms) in between. In one aspect, the monomer may have up to five functional groups. A functional group includes, but is not limited to acrylates, methacrylates, thiols, alkenes (i.e., vinyl ether and vinyl ester).

By way of a second example, in one aspect, the monomer is a 3-chlorophenyl acrylate (CPA) as exhibited by Structure B below:

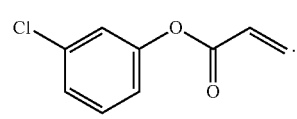

Structure B

As a third example, in another aspect, the monomer of the chemical composition is a 2,4-dichlorophenyl acrylate (DCPA) as shown below in Structure C:

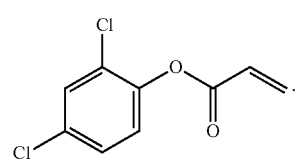

Structure C

As a fourth example, in one aspect, the monomer is a 4-bromophenyl acrylate (BPA) as shown below in Structure D.

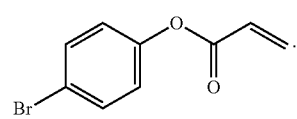

Structure D

As a final example, in another aspect, the monomer is a 2,4-dibromophenyl acrylate (DBPA) as depicted in Structure E below:

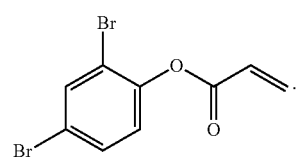

Structure E

When the aforementioned examples (Structures A-E) are incorporated into a polymerizable formulation of any mixture of initiators, monomers, oligomers, reactive diluents and other additives (e.g., an acrylate based coating), as is well known in the art, the monomers, oligomers and reactive diluents can be polymerized. The addition of an initiator begins the free-radical, cationic, or anionic polymerization when initiated by exposure to an energy source. The curing mechanism may be accomplished by many different energy sources including, but not limited to, ultraviolet radiation (UV), visible radiation, infrared radiation (IR), electron beam, or microwave radiation. The polymer forms a cross-linked structure that may resemble a "fish-net" as some monomers as described above are multifunctional (e.g., have more than one C=C group). The polymeric structure, in one embodiment where CPA is copolymerized with 1,6-hexanediol diacrylate (HDODA), is represented below as Structure F where the boldfaced "zigzagged" lines represent continued polymerization with randomly polymerized CPA or HDODA:

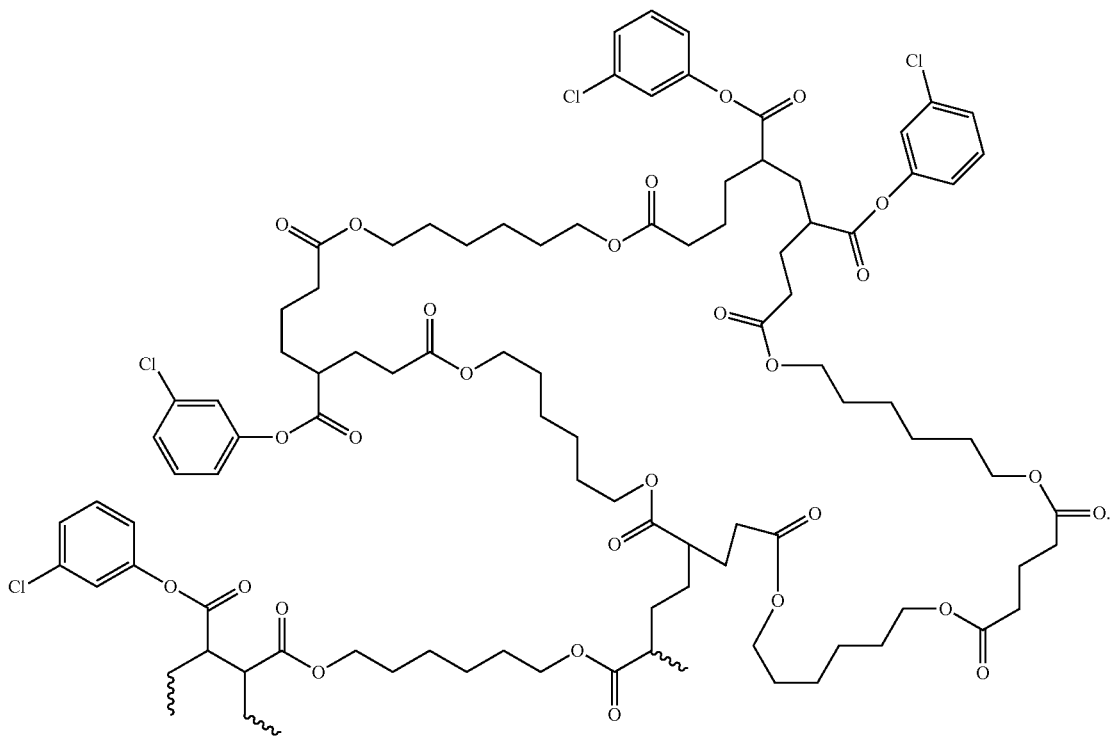

Structure F

The polymeric composition forms a surface with the smoothness approximating that of electropolished (e.g., pharmaceutical and/or surgical grade) steel; the attachment of microorganisms to the surface is thereby compromised, making the surface resistant to the formation of biofilms.

In addition, the curable monomeric composition of the invention is relatively safe when polymerized (i.e., cured) completely into the polymeric matrix, even for widespread use, due to the polymer's inability to diffuse into and adversely affect the vast majority of multi-cellular organisms' (e.g., plants and animals) biological functions.

Moreover, because the effective groups of the present invention are attached by covalent bond, the polymerized composition does not "leach" materials into its surrounding environment. This enhances the durational efficacy and safety of the material incorporating the polymer of the present invention polymerized onto or into the substrate.

Surfaces and substrates treatable with the compositions of the present invention include, but are not limited to, textiles, carpet, carpet backing, upholstery, clothing, sponges, plastics, metals, medical devices of silicone, polyurethane, PVC and the like for drainage tubing, dialysis and urinary catheters, biliary tubing and biliary stents, feeding tubes, medial hydrogels, topical and transdermal carrier applications, biodegradable hydrogels with topical and internal applications, surgical dressings, anti-microbial anti-fog sheets, greenhouse sheeting, freezer doors, masonry, silica, sand, alumina, aluminum chlorohydrate, titanium dioxide, calcium carbonate, wood, glass beads, containers, tiles, floors, curtains, marine products, tents, backpacks, roofing, siding, fencing, trim, insulation, wall-board, trash receptacles, outdoor gear, water purification systems, and soil. Furthermore, articles treatable with the compositions of the present invention include, but are not limited to, cabinetry, countertops, natural and artificial wood flooring, floor tiles, bathroom tiles, faucets, sinks, showers, bathtubs, pools, toilets, air filters and materials used for the manufacture thereof, aquarium filters, buffer pads, fiberfill for upholstery, fiberglass duct-board, underwear and outerwear apparel, polyurethane and polyethylene foam, sand bags, tarpaulins, sails, ropes, shoes, socks, towels, disposal wipes, hosiery, feminine hygiene products and intimate apparel; cosmetics, lotions, creams, ointments, disinfectant sanitizers, wood preservatives, plastics, adhesives, paints, pulp, paper, cooling water, and laundry additives and non-food or food contacting surfaces in general. Other examples include general odor control in clothing, antimicrobial band aid design, protective barrier materials in animal care including mastitis control, clean room design and wall treatments in food handling rooms.

Other features and advantages of the present invention will be apparent from the following detailed description and claims.

BRIEF DESCRIPTION OF THE DRAWINGS

FIG. 4 is a qualitative quantification of bacterial growth on a thermoplastic polymer surface in a LB agar broth of *E. coli* and the same growth on the composition of the present invention. This measurement was taken from one milliliter of the coli broth cultured at 37° C. for 24 hours on top of a coating incorporating the present invention. Biofilm resistance testing results after *E. coli* growth and staining where each plate was treated with a varied concentration of the *E. coli* broth: A diluted 1:3 broth to sterile, deionized water, B was a 1:1 dilution, C was a 3:1 dilution, and D was the undiluted broth (approximately $10^9$ cells/mL).

DETAILED DESCRIPTION OF THE INVENTION

Figure 1:
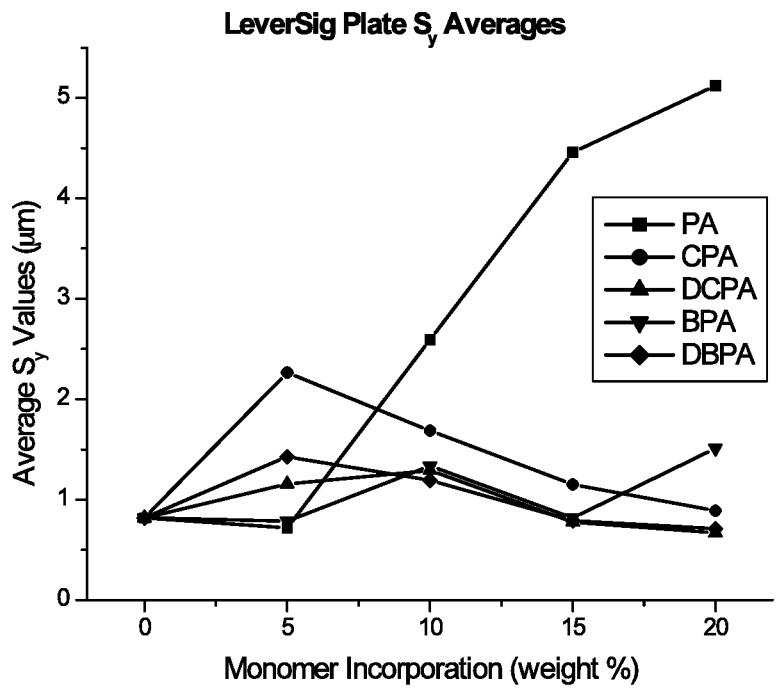
FIG. 1 is a graphical illustration of measurements of the average roughness of exemplary compositions as a value of $S_y$ (the peak to valley distance) in micrometers (μm). The LeverSig Plate is representative of an accepted method of measuring roughness, as is known in the art. Each composition was plated at a coating level of 20, 15, 10 and 5 weight percent of the monomer tested. The compositions tested are labeled as their monomer components: 4-bromophenyl acrylate (BPA), 3-chlorophenyl acrylate (CPA), 2,4-dibromophenyl acrylate (DBPA), 2,4-dichlorophenyl acrylate (DCPA), and phenyl acrylate (PA).
Figure 1:
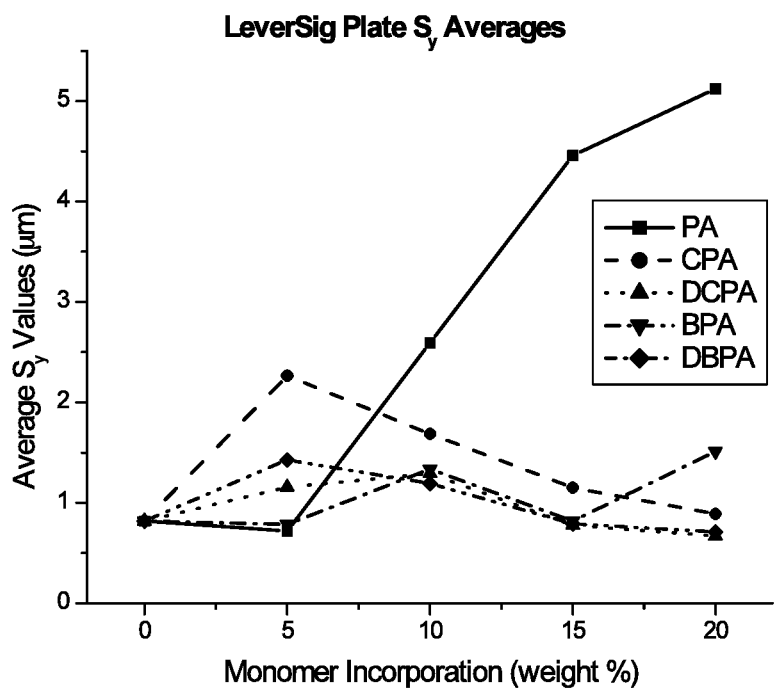

For convenience, certain terms employed in the specification, examples, and appended claims are described below.

The term "alkene-based monomers" is defined as compounds comprised, in part, of a carbon-carbon double bond (i.e., C═C) which may react via a free-radical, cationic, and/or anionic mechanism thereby forming long chain, branched, and/or crosslinked polymers (i.e., high molecular weight molecules having the qualities of 1) chain entanglement, 2) additive intermolecular forces, and 3) long range molecular interactions all of which contribute to the physical and chemical properties of the whole polymer (See Structure G).

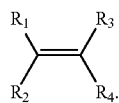

Structure G

Typically, alkene-based monomers are comprised of zero (e.g., ethylene), one, two, or three substituents. Monosubstituted alkene-based monomers (i.e., those where $R_1$ comprises an organic or inorganic substituent) are most common followed by 1, 1-disubstituted alkene-based monomers (i.e., those where $R_1$ and $R_2$ comprise an organic or inorganic substituent). Trisubstituted alkene-based monomers (i.e., those where $R_1$, $R_2$, and $R_3$ comprise an organic or inorganic substituent) and tetrasubstituted alkene-based monomers are least common due to reduced reactivity of the C═C to polymerization. Examples of substituents include alkanes, cycloalkanes, alkenes, cycloalkenes, alkynes, cycloalkynes, alkyl halides, aryl halides, aromatic hydrocarbons, aromatic heterocycles, polycyclic aromatic compounds (hydrocarbon or heterocyclic), alcohols, phenols, ethers, epoxides, thiols, sulfides, aldehydes, ketones, carboxylic acids, nitriles, acid halides, acid anhydrides, amides, esters, thioesters, amines, or any combination thereof.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone for straight chain, and more preferably 20 or fewer. Likewise, preferred cycloalkyls have from 3-10 carbon atoms in their ring structure, and more preferably have 5, 6 or 7 carbons in the ring structure.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, amino, imido, amido, lactams, phosphonate, phosphinate, carbonyl, carboxyl, silyl, thiol, ether, alkylthio, sulfonyl, sulfonamido, ketone, aldehyde, ester, thioester, lactones, heterocyclyl, aromatic or heteroaromatic moieties, trifluoromethyl, nitrile, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The term "bioavailable" is meant to refer to an appropriate location, orientation or formulation of a compound for performance of the compound's bioactivity.

"Biofilm" refers to an accumulation of organisms on a surface (e.g. bacteria archaea, fungi, molds, algae, or protozoa). A mature biofilm can comprise a colony of microorganisms resident upon a surface surrounded by an exopolysaccharide.

"Biofllm resistant" or "antifouling" or "AF" refers to inhibition or decrease in the amount of biofouling organisms that attach and/or proliferate.

A "biofoul or biofilm resistant coating" refers to any coating (as defined herein) that impairs, inhibits, prevents or retards the attachment and/or growth of biofouling organisms.

The term "carbonyl" refers to a carbon double condedt o an oxygen (i.e., C═O) with two other substituents on the carbon and is art recognized by practitioners in the field. Examples of substituents include alkanes, cycloalkanes, alkenes, cycloalkenes, alkynes, cycloalkynes, alkyl halides, aryl halides, aromatic hydrocarbons, aromatic heterocycles, polycyclic aromatic compounds (hydrocarbon or heterocyclic), alcohols, phenols, ethers, epoxides, thiols, sulfides, aldehydes, ketones, carboxylic acids, nitriles, acid halides, acid anhydrides, amides, esters, thioesters, amines, or any combination thereof. The only stipulation is that at least one of the substituents must be a polymerizable alkene or thiol or be partially comprised of a polymerizable alkene or thiol.

A "coating" refers to any temporary, semipermanent or permanent layer, covering or surface. A coating can be a gas, vapor, liquid, paste, semi-solid or solid. In addition a coating can be applied as a liquid and solidify into a hard coating. Examples of coatings include polishes, surface cleaners, caulks, adhesives, finishes, paints, waxes, and polymerizable compositions (including phenolic resins, silicone polymers, chlorinated rubbers, coal tar and epoxy combinations, epoxy resin, polyamide resins, vinyl resins, elastomers, acrylate and methacrylate polymers, fluoropolymers, polyesters and polyurethanes, latex). Silicone resins, silicone polymers [e.g., room-temperature-vulcanizing (RTV) polymers] and silicone heat cured rubbers are suitable coatings for use in the invention and described for example in the Encyclopedia of Polymer Science and Engineering (1989) 15: 204 et seq. Coatings can be biodegradable, ablative, or dissolvable, so that the dissolution rate of the matrix controls the rate at which AF agents are delivered to the surface. Coatings can also be non-ablative, and rely on diffusion principles to deliver a separate AF agent to the surface. Non-ablative coatings can be porous or non-porous. A coating containing an AF agent freely dispersed in a polymer binder is referred to as "monolithic" coating. Elasticity can be engineered into coatings to accommodate pliability, e.g., swelling or shrinkage, of the surface to be coated. Coatings can be non-leaching and durable over extended time points.

A "delivery system" refers to any system or apparatus or component whereby therapeutic, including other antifouling compounds can be delivered from the surface upon which biofilm formation is to be inhibited, by coating the surface with, the present invention. Other mechanisms comprising delivery systems will be apparent to those of skill in the relevant arts.

"Dressing" refers to any bandage or covering applied to a lesion or otherwise used to prevent or treat infection. Examples include wound dressings for chronic wounds (such as pressure sores, venous stasis ulcers and burns) or acute wounds and dressings over percutaneous devices such as IVs or subclavian lines intended to decrease the risk of line sepsis due to microbial invasion. For example, the compounds and compositions of the present invention could be applied to or incorporated in the adherent dressing material applied directly over the entry site.

The phrase "effective amount" refers to an amount of the disclosed antifouling compounds that significantly reduces the number of organisms that attach to a defined surface, relative to the number that attach to an untreated surface. An effective amount of the disclosed antifouling compound is said to inhibit the formation of biofilms, and to inhibit the growth of organisms on a defined surface. The term "inhibit," as applied to the effect of an antifouling compound on a surface, includes any action that significantly reduces the number of organisms that attach thereto.

"Functional groups" are specific groups of atoms within molecules that are responsible for the characteristic chemical reactions of those molecules. The same functional group will undergo the same or similar chemical reaction(s) regardless of the molecule's size of which it is a part.

The term "health-related environment" is understood to include all those environments where activities are carried out that are implicated in the restoration or maintenance of human health. A health-related environment can be a medical environment, where activities are carried out directly or indirectly intended to restore human health. An operating room, a doctor's office, a hospital room, and a factory making medical equipment are all examples of medical environments. Other health-related environments can include industrial or residential sites where activities pertaining to human health are carried out. Such activities include food processing, water purification, and sanitation.

A "household item" includes items used within a home, or contained therein. For example, household items would include, walls, flooring, furniture, countertops, sinks, faucets, baths, toilets, cabinetry, shelving, appliances (kitchen and otherwise), toys, and the like.

The term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

An "implant" is any object intended for placement in a human body that is not a living tissue. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body.

The terms "infectious microorganisms" or "infectious agents" as used herein refers to disease causing or contributing bacteria (including gram-negative and gram-positive organisms, such as Staphylococci sps. (e.g., *Staphylococcus aureus, Staphylococcus epidermis*), *Enterococcus* sps. (e.g., *E. faecalis*), *Pseudomonas* sp. (*P. aeruginosa*), *Escherichia* sps. (e.g., *E. coli*), *Proteus* sps. (e.g., *P. mirabilis*), fungi (including *Candida albicans*), viruses, and protists.

"Medical device" refers to a non-naturally occurring object that is inserted or implanted in a subject or applied to a surface of a subject. Medical devices can be made of a variety of biocompatible materials including metals, ceramics, polymers, gels, and fluids not normally found within the human body. Medical devices can also be fabricated using certain naturally-occurring materials or treated naturally-occurring materials. As an example, a heart valve can be fabricated by combining a treated porcine heart valve with an affixation apparatus using artificial materials. Medical devices can include any combination of artificial materials, combinations selected because of the particular characteristics of the components. For example, a hip implant can include a combination of a metallic shaft to bear the weight, a ceramic artificial joint and a polymeric glue to affix the structure to the surrounding bone. An implantable device is one intended to be completely imbedded in the body without any structure left outside the body (e.g., heart valve). An insertable device is one that is partially imbedded in the body but has a part intended to be external (e.g., a catheter or a drain). Medical devices can be intended for short-term or long-term residence where they are positioned. A hip implant is intended for several years of use, for example. By contrast, a tissue expander may only be needed for a few months, and is removed thereafter. Insertable devices tend to remain in place for shorter times than implantable devices, in part because they come into more contact with microorganisms that can colonize them.

"Substrate" means any surface on which a biofilm can form or has formed. Substrate includes, but is not limited to, hard or soft surfaces such as polymers, plastics, tubing, ceramics, cellulosic materials (e.g., wood and paper), metals, glass, concrete, hydroxyapatite, skin, bone, or tissues.

The term "surface," as used herein, refers to any surface whether in an industrial or a medical setting that provides an interface between an object and a fluid, permitting at least intermittent contact between the object and the fluid. A surface, as understood herein, further provides a plane whose mechanical structure, without further treatment, is compatible with the adherence of microorganisms. Surfaces compatible with biofilm formation may be smooth or irregular. Fluids contacting the surfaces can be stagnant or flowing, and can flow intermittently or continuously, with laminar or turbulent or mixed rheologies. A surface upon which a biofilm forms can be dry at times with sporadic fluid contact, or can have any degree of fluid exposure including total immersion. Fluid contact with the surface can take place via aerosols or other means for air-borne fluid transmission.

Biofilm formation with health implications can involve those surfaces in many environments, including surfaces found in medical environments and those surfaces in industrial or residential environments that are involved in those functions essential to well-being like nutrition, sanitation and the prevention of disease. By reference to industrial and residential setting, biofilm formation on contact-items where microorganisms can infect by skin-surface contact is an area of concern. Biofilm formation can be evident household items including: floors, walls, appliances, furniture, toys, and the like.

Biofilm formation can be evident on the surfaces of household items. Infection by microorganisms in the biofilm may occur with skin-surface contact. Household items susceptible to biofilm formation, which may be coated with the compositions of the present invention, include: flooring (e.g., vinyl, laminate, wood, stone, carpeting (wool, synthetic, polyester, polypropylene, etc.), tile, etc.), walls (e.g., drywall, wallpaper, paints, etc.), furniture (e.g., plastics, woods, laminates, ceramics, metals, glass, upholsteries, etc.), toys (e.g., plastics, woods, ceramics, cloth, metals, glass, etc.), appliances (e.g., toasters, microwave ovens, conventional ovens, washers, dryers, dishwashers, mixers, food processors, etc.), electronic appliances (e.g., DVRs, DVD players, televisions, computers, keyboards, mouses, cable boxes, remote controllers, MP3 players, stereo systems, etc.), communication devices (e.g., phones, earpieces for phones, etc.), kitchen fixtures (e.g., sinks and associated hardware, faucets, etc.), bathroom fixtures (e.g., baths and associated hardware, showers and associated hardware, sinks and associated hardware, faucets, toilets and associated hardware, etc.), electrical switch plates and outlets, lighting, doors and associated hardware, railings and associated posts, trash cans, and other surfaces found in homes.

Similarly, biofilm formation may be encountered on surfaces of commonly visited public places. Such surfaces may negatively impact the health of an individual who contacts the biofilm by skin contact. Such public use surfaces include: shopping carts, shelving, cash registers, key pads commonly used for credit card purchases, touch screens and other electronic equipment, conveyor belts, playground equipment, public drinking fountains, flooring (e.g., carpet or otherwise), walls, public restrooms (e.g., urinals, toilets, sinks, hand dryers (e.g., paper, cloth and air), faucets, walls and flooring contained therein, stalls, toilet paper dispensers, trash containers, feminine hygiene containers, dispensing machines, soap dispensers, etc.), railings and their associated posts, and other similar surfaces.

Biofilm formation may occur on other everyday residential and industrial items. Such items may also incorporate the compositions of the present invention into or onto the substrate. Surfaces included as residential and industrial items are: vehicles (interior and exterior), carseats, lawn maintenance equipment (e.g., lawn mowers, edgers, clippers, weed-wackers, etc.), gardening equipment (e.g., shovels, spades, etc.), industrial equipment, tools both residential and industrial (e.g., wrenches, screwdrivers, drills, vices, etc.), concrete structures, and other items used in residential and industrial settings composed of the materials outlined above (e.g., waxes, liquids, polymers, plastics, woods, ceramics, glass, metals, etc.).

Coatings of the present invention can also be suitable in military applications, such as protection against biological warfare, self-decontamination of war planes, cargo and shipping boxes, envelopes, uniforms, army ducts and the like.

A surface of an article adapted for use in a medical environment can be capable of sterilization using autoclaving, biocide exposure, irradiation or gassing techniques like ethylene oxide exposure. Surfaces found in medical environments include the inner and outer aspects of various instruments and devices, whether disposable or intended for repeated uses. Such surfaces may incorporate the compositions of the present invention into or onto the substrate. Examples include the entire spectrum of articles adapted for medical use, including scalpels, needles, scissors and other devices used in invasive surgical, therapeutic or diagnostic procedures, implantable medical devices (including artificial blood vessels, catheters and other devices for the removal or delivery of fluids to patients), artificial hearts, artificial kidneys, orthopedic pins, plates and implants, catheters and other tubes (including urological, biliary, and endotracheal tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts), prostheses (including breast implants, penile prostheses, vascular grafting prostheses, heart valves, artificial joints, artificial larynxes, ontological implants), vascular catheter ports, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. These surfaces also may incorporate the compositions of the present invention into or onto the substrate. Such surfaces can include countertops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinylic materials, similar to the polymerized form of the present invention, are commonly for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

Surfaces in contact with liquids are particularly prone to biofilm formation, and may incorporate the compositions of the present invention into or onto the substrate. As an example, those reservoirs and tubes used for delivering humidified oxygen to patients can bear biofilms inhabited by infectious agents. Dental unit waterlines similarly can bear biofilms on their surfaces, providing a reservoir for continuing contamination of the system of flowing and aerosolized water used in dentistry.

Sprays, aerosols and nebulizers are highly effective in disseminating biofilm fragments to a potential host or to another environmental site, and may be coated with the present invention. It is understood to be especially important to health to prevent biofilm formation on those surfaces from whence biofilm fragments can be carried away by sprays, aerosols or nebulizers contacting the surface.

Other surfaces that may incorporate the compositions of the present invention into or onto the substrate related to health include the inner and outer aspects of those articles involved in water purification, water storage and water delivery, and those articles involved in food processing.

Surfaces amenable to incorporating the compositions of the present invention into or onto the substrate to render such surfaces resistant to biofilm formation are vast and many. Other surfaces not specifically named above may be coated with the present invention, as would be apparent to one skilled in the art.

"Tertiary amines" are nitrogen-containing compounds wherein three substituents are bonded to the nitrogen (See Structure H).

Structure H

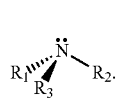

Examples of substituents include alkanes, cycloalkanes, alkenes, cycloalkenes, alkynes, cycloalkynes, alkyl halides, aryl halides, aromatic hydrocarbons, aromatic heterocycles, polycyclic aromatic compounds (hydrocarbon or heterocyclic), alcohols, phenols, ethers, epoxides, thiols, sulfides, aldehydes, ketones, carboxylic acids, nitriles, acid halides, acid anhydrides, amides, esters, thioesters, amines, or any combination thereof. Typically, multiply-bonded nitrogens having double or triple bonds are not considered tertiary amines because they often exhibit chemical properties distinctly different than the previously defined tertiary amines.

A "thermoplastic polymer" is a polymer consisting of long chain and/or branched molecules wherein weak intermolecular forces may be overcome by the addition of heat to form a polymer melt (i.e., liquid) that can then be molded, formed, blown, extruded, etc. into a variety of forms upon cooling and formation into a solid including, but not limited to, fibers, hard plastic parts, films, etc. Thermoplastic polymers may be dissolved, recycled, reused, recombined, etc. after their formation and, when complete, maintain their physical and chemical properties from before the addition of heat or solvent.

A "thermoset polymer" is a polymer consisting of long chain and/or branched molecules that may or may not be crosslinked have chemical bonds linking individual chains to one another to form a molecular "net" or "mesh") wherein strong intermolecular forces and/or crosslinking may not be overcome by the addition of heat to form a polymer melt. The addition of excess heat to a thermoset polymer most often causes the polymer to irreversibly degrade to an unusable material devoid of its previous physical and chemical properties present in its polymeric form. In other words, thermoset polymers, unlike thermoplastic polymers, cannot be dissolved, recycled, reused, recombined, etc. after their formation. Instead, thermoset polymers must be polymerized in a mold (e.g., polyurethane foams, Fiberglas, etc.), in the extrusion process (e.g., Kevlar, Nomex, etc.), on a surface (e.g., coatings, adhesives, inks, etc.), or other methodology to form the desired material. Additionally, some thermoset polymers may be machined after formation (e.g., wood, Fiberglas, etc.) to form other more pragmatic products.

For purposes of this invention, the chemical elements are identified in accordance with the Periodic Table of the Elements, CAS version, Handbook of Chemistry and Physics, 67th Ed., 1986 87, inside cover.

Compositions of the Invention

In certain embodiments, the present invention is a polymerizable (i.e., curable) monomeric composition, having the general Structure A, shown above, that may be polymerized onto (e.g., coating) or into (e.g., as a comonomer in a thermoplastic or thermoset polymer matrix) a contact substrate, which may include medical devices and other products. In this embodiment, R', R", or R'" represents a halogen (e.g., Chlorine or Bromine), Hydrogen, or other organic moiety (e.g., alkyl, aryl, etheric, esteric, amido, amino, thiyl, or other hydrocarbon- or heteronuclear-based functional group) as long as at least one substituent (R', R", R'") is a halogen, R"" represents either a Hydrogen or a Methyl (e.g., $CH_3$) group, and Z represents an Oxygen or other organic moiety as previously defined where one Oxygen binds the organic moiety to the aryl group and another Oxygen binds the organic moiety to the carbonyl adjacent to the depicted alkene. Furthermore, the monomer may be mono- or multi-functional in the number of polymerizable groups (e.g., acrylic or methacrylic groups). The active component of the monomer is its phenyl ring with halogens. The monomer can be covalently bonded to any polymerizable functional group with or without a spacer group (i.e., other atoms) in between. In one aspect, the monomer may have up to five functional groups. A functional group includes, but is not limited to acrylates, methacrylates, thiols, and alkenes (i.e., vinyl ether and vinyl ester).

For example, where the monomer is a phenyl acrylate (PA) with the structure below, Structure I, no biofilm inhibitory activity is present:

Structure I

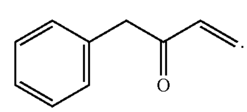

In this example, the Z is an Oxygen, R', R", R'", and R"" are Hydrogens. Because no halogens are in those positions, as enumerated above, PA is biologically inactive and, as such, was used as an internal standard or control to demonstrate that halogenation induces biological activity.

In other preferred embodiments, the monomer is a 3-chlorophenyl acrylate (CPA) as exhibited by Structure B, above, wherein Z is an Oxygen, R" is a Chlorine, and R', R'", and R"" are Hydrogens. As a third example, in another embodiment, the monomer of the chemical composition is a 2,4- dichlorophenyl acrylate (DCPA) as shown in Structure C above. In this embodiment Z is an Oxygen, R' and R''' are Chlorines, and R'' and R'''' are Hydrogens. In yet another embodiment, the monomer is a 4-bromophenyl acrylate (BPA) as shown above in Structure D wherein Z is an Oxygen, R''' is a Bromine, and R', R'', and R'''' are Hydrogens. Another embodiment uses a monomer that is a 2,4-dibromophenyl acrylate (DBPA) as depicted in Structure E above. DBPA has an Oxygen in the Z location, Bromines as R''' and R', and Hydrogens at R'' and R''''.

The monomers are polymerized into a vinylic (i.e., alkene having a polymerizable C=C) containing formulation, as is well known in the art. The addition of an initiator that begins the free-radical, cationic, or anionic polymerization initiated by an energy source; however, in certain cases, the polymerization does not need a separate initiator molecule to begin the polymerization, as is the case, for example, with electron beam technology or other technologies well known to practitioners of the art. The curing mechanism may be accomplished by many different energy sources including, but not limited to, ultraviolet radiation (UV), visible radiation, infrared radiation (IR), electron beam, or microwave radiation. The polymer forms a crosslinked structure that may resemble a "fish-net" as some monomers as described above are multifunctional (e.g., have more than one C=C group). The polymeric structure, in one embodiment, is represented as Structure F shown above.

The polymeric composition can form a surface with the smoothness approximating that of electropolished (e.g., pharmaceutical and/or surgical grade) steel. Such smoothness, a physical phenomenon, interferes with the ability of various microorganisms to attach to a surface coated with the polymeric composition. Interference with attachment, an initial required step for biofilm formation, renders such surfaces resistant to the formation of biofilms. Other reasons for the inhibition of biofilm formation by the claimed polymeric composition could include: 1) the lack of a proper food source and 2) improper surface chemistry for microbial attachment, a chemical phenomenon.

Biofilm Inhibitory Utilities

By interfering with the attachment of microorganisms to a surface, the presently claimed composition has broad applicability in effectively inhibiting the development of biofilms on household items, residential, industrial, and health related surfaces.

In one embodiment, compositions of the present invention may be incorporated into or adhered to a variety of household items and appliances. For example, the biofilm resistant polymer herein disclosed may be adhered to or incorporated into children's toys. Children's toys axe made of a variety of materials including: plastics, polymers, woods, metals, glass, cloth and the like. Moreover, these toys are often subject to regular mouth-contact with the child-user. Biofilm formation on such items can lead to infection of the child when, inevitably, skin to surface or mouth to surface contact occurs. Incorporating the compositions of the present invention into or onto the substrate of such objects may reduce the risk of infection and subsequent health consequences on the child. In contrast to currently used sanitization methods that employ the application of fluid or wipes with antibacterial properties, the compositions of the present invention are relatively permanent and durable in nature, and reapplication is not necessary. Moreover, the covalent bond nature of the compositions of the present invention ensure that no or very limited "leaching" of chemicals is present from application of the biofilm resistant polymer to the toys. Thus, users of the present invention may be confident that microorganism attachment to their child's playthings is controlled, and the child will not be exposed to harmful amounts of any antibacterial or biofilm resistant chemicals by contact with the toy.

Similarly, coating objects that are consistently contacted by individuals may reduce infection by biofilm organisms and benefit the health of individuals. In another example, shopping carts are subject to multi-individual use through one day, and often are handled by the hands or mouths of children. Currently, many vendors provide antibacterial wipes to minimize the risk of infection from handling shopping carts. These antibacterial wipes may contain harsh ingredients, impart chemicals onto the cart, and may not be effective in eliminating all microorganisms that can negatively impact the health of the user. Moreover, markets exist that provide a shield between a child seated within the cart and the cart itself. Incorporating the compositions of the present invention into or onto the substrates of a shopping cart may provide superior biofilm resistance by prohibiting the attachment of microorganisms. Thus, the user need not treat the shopping cart with chemicals before handling, and shields between a child and the cart would be unnecessary. Again, because the present invention is relatively non-leaching and permanent and is durable, users can be confident that no toxic amounts of deleterious chemicals will be imparted to them, or any occupants seated in the cart.

Phones are well known harborers of microorganisms that transmit sickness to users including the common cold and flu. Following the same rationale above, the present invention can be incorporated onto or into such devices to minimize or eliminate transference of such microorganisms from the phone to its user. Because most users do not regularly sanitize objects such as their phone, a material comprised of the present invention could have significant impact in reducing infection from the phone to its user. Similar objects, including: MP3 players, handheld organizers, remote controllers, and video game materials, can incorporate the present invention to minimize infection by skin-contact with such items.

Other objects commonly contacted by individuals in the home or otherwise can benefit from coating or incorporation of with a composition of the present invention. By way of examples within the household, key pads for appliances, appliances themselves, computers and associated hardware, cabinetry, in particular keyboards and mouses can harbor biofilms that can infect users. Especially where multiple users contact the object, coating with or incorporating the present invention can minimize spread of microorganisms from one user to the next.

The present invention is especially applicable where items in places frequented by the public may be contacted by multiple individuals. Some items that may be coated with the compositions of the present invention to reduce biofilm formation include: seating (e.g., benches, movie theater, transportation, and stadium), play grounds and equipment, flooring and walls, etc. Because of the adherent nature of the present invention most surfaces may be coated with or have the present invention incorporated into the substrate material itself, providing added protection against microorganism adherence and colonization. As stated earlier, the durable, relatively permanent, and relatively non-leaching nature of the compositions of the present invention make their use cost-effective and safe for repeated contact by individuals, while minimizing exposure to potentially health threatening microorganisms.

Other surf-aces that bear specific mention in the residential and industrial arena axe those found in bathrooms. While it is well-known that toilets and their associated hardware and surrounding surfaces are particularly susceptible to infestation by microorganisms, it should be noted that sinks and their associated hardware are more likely to contain biofilms that can negatively impact the health of a user. Adherence of the present invention to such surfaces, including flooring, walls, and fixtures can provide a system for controlling the colonization and spread of biofilms. This can be especially important where the public or multiple users employ the toilets, sinks, faucets and the like. By coating such surfaces with a composition of the present invention the build-up of microorganisms that create biofilms can be attenuated, thereby decreasing the instance of infection to a user by contact with such surfaces.

The compounds of the present invention may be incorporated into pools, fountains, aquariums and the like, whether they are constructed from cement, a plastic derivative or the like. Biofilm formation in such areas where water remains in a container is notorious and well known. Coating the surfaces or incorporating the compounds of the present invention may inhibit biofilm formation on such materials, thereby reducing time cleaning or chemicals used for sanitizing such containers. Especially where the public frequents fountains or pools, use of the present invention could reduce infection transferred to persons from biofilm formation on those materials.

In one embodiment, the compositions of the present invention may be applied to or incorporated into industrial surfaces, including as metals, ceramics, thermoplastics or thermoset polymers, elastomers, PVC, glass or wood to prevent biofilm formation. Application to such surfaces may decrease infection by contact of individuals, and could thereby increase efficacy of production where fewer employees and customers suffer sickness due to infection by microorganisms that would otherwise adhere to and colonize such surfaces. Moreover, products manufactured by equipment incorporating the compositions of the present invention into or onto the substrate are less likely to contain biofilms. For example, where products manufactured in the food packaging industry are coated with or incorporate (i.e., as a comonomer) compositions of the present invention, resistance to biofilm formation may be conferred to those products, decreasing spoilage. Additionally, machinery used in the food packaging industry can benefit from coating with the biofilm resistant polymers of the present invention, increasing efficiency by decreasing time sanitizing machinery, and decreasing the instance of fouling of the foods processed by those machines. Furthermore, using the present invention in the restaurant industry (e.g., countertops, flatware, silverware, dishes, tables, chairs, serving trays, etc.) on materials that come into contact with the food preparation process and where consumers are present could reduce the risk of food-borne or similar illness of customers and employees.

The compositions of the present invention may be incorporated into indoor paints, thus decreasing biofilm formation on surfaces using such paints. This could have a significant impact in decreasing infection from skin-contact interaction with those surfaces.

Compositions of the invention may be employed in concrete structures used to house animals in the industrial setting. Biofilm formation in such structures is well known and is the cause of infection that compromises the health of livestock and fowl. Rendering surfaces of such structures, whether they be constructed of concrete, metal, wood or the like could significantly reduce the formation of biofilms and subsequently decrease the likelihood of infection in such settings. A decrease of infection of such livestock and fowl not only provides economic advantage, but also increases their safety for consumption by end users.

In addition, for household use, compounds of the invention can be incorporated into ointments to protect injured areas and to protect intact skin from prolonged microbial exposure. As an example, a topical compound of the invention can inhibit the development of fungal infections like athlete's foot; the agent can be dispensed as a cream, an ointment, a powder or a spray. Other preparations can be used in moist areas to inhibit local yeast infections. Applying a compound of the invention to the materials used for fabricating menstrual tampons may inhibit the formation of those *Staphylococcal* species responsible for toxic shock syndrome.

For example, wounds where skin grafts or skin substitutes are particularly adapted for the application of the compositions of the present invention and should reduce the tendency for infectious organisms to accumulate without impacting the general healing process. Formulation of such a preparation is consistent with the skill of ordinary practitioner in these arts.

Compounds of the invention can be formulated as a solution suitable for applying to skin surfaces that will form a durable film that can remain in place over a sustained period of time. Such a solution could be applied to the hands of medical personnel underneath surgical gloves to reduce the contamination hazards from glove tears. Such a solution could also be applied to exposed skin surfaces, for example the uncovered face, of medical personnel in settings where contaminated splashes are likely.

Naturally derived processed materials commonly are positioned in the body in order to provide a structure for ingrowth of the patient's own tissues. Examples include demineralized bone materials and hydroxyapatite. These materials themselves are non-living and avascular. Colonization of these materials with microorganisms and biofilm formation can require their removal, reducing or ablating the ability of the patient to heal. Incorporating the compositions of the present invention into or onto the substrate can enhance their resistance to biofilm formation and its consequences.

Certain naturally derived processed materials will be determined by artisans in these fields to be especially suitable for the coating of with compositions of the present invention. Fibrillar preparations can permit the fibers to be coated with the compound. Solid articles such as reconstructive blocks of hydroxyapatite can be painted with a coating of the compound for additional protection.

Implantable medical devices, using artificial materials alone or in combination with naturally-derived materials, can be treated with compositions of the present invention either by surface coating or by incorporation. Metals may be suitably treated with surface coats while retaining their biological properties. Certain embodiments treated in this manner may be suitable for orthopedic applications, for example, pins, screws, plates or parts of artificial joints. Methods for surface treatment of metals for biological use are well-known in the relevant arts. Other materials besides metals can be treated with surface coats of compounds according to the present invention as the medical application requires.

Implantable devices may comprise materials suitable for coating or incorporating the present invention into those surfaces with the compositions of the present invention. Embodiments whose components may be coated with compositions of the present invention can include polymers, ceramics and other substances. Bioabsorbable materials such as poly(glycolic acid) and poly(lactic acid) polymers can be used to fabricate sutures and orthopedic devices. Those of ordinary skill in these arts will be familiar with techniques for incorporating the present invention onto the polymers used to shape formed articles for medical applications. Compositions of the present invention may be incorporated into glues, cements or adhesives, or in other materials used to fix structures within the body or to adhere implants to a body structure. Examples include poly(methyl methacrylate) and its related compounds, used for the affixation of orthopedic and dental prostheses within the body. The presence of the composition of the instant invention can decrease biofilm formation in those structures in contact with the glue, cement, or adhesive. A composition of the invention can coat or can permeate the formed article. By coating, the biofilm resistant polymer prevents and/or minimizes adherence and colonization of microorganisms responsible for biofilm formation. Materials incorporating compounds are adaptable to the manufacture of a wide range of medical devices, some of which are disclosed below. Other examples will be readily apparent to those practitioners of ordinary skill in the art.

In one embodiment, compositions of the invention can be applied onto or incorporated in certain medical devices that are intended to be left in position permanently to replace or restore vital functions. As one example, ventriculoatrial or ventriculoperitoneal shunts, and dialysis shunts may be coated with compositions of the present invention. Dialysis shunts are especially susceptible to the formation of biofilms and subsequent infection and may be a part of a lifelong process, making it desirable to prevent the attachment and colonization of microorganisms that can form biofilms.

Heart valves comprising artificial material are understood to be vulnerable to the dangerous complication of prosthetic valve endocarditis. Artificial heart valves coated with the compositions of the invention may reduce the incidence of primary and recurrent prosthetic valve endocarditis caused by biofilm formation. Compositions of the invention can be applied to the synthetic portions or the naturally-derived portions of heart valves.

Pacemakers and artificial implantable defibrillators commonly comprise metallic parts in combination with other synthetic materials. These devices may be coated with compositions of the invention to reduce biofilm formation, which necessitates removal and replacement of the medical device.

Devices implanted into the body either temporarily or permanently to pump pharmacological agents into the body can comprise metallic parts in combination with other synthetic materials. The device may be partially or entirely covered with the compositions of the present invention, thereby reducing the risk of contamination and subsequent infection.

Additionally, various vascular grafting prostheses and stoats intended to bypass blocked arteries or substitute for damaged arteries may employ compositions of the present invention. Vascular grafting prostheses, made of poly(tetrafluoroethylene), polyethylene tere-phthalate), expanded poly(tetrafluoroethylene) (e-PTFE), and related materials, are available for use on any major blood vessel in the body and may be coated with or covalently incorporate the compositions of the present invention. Stents comprising metallic frames covered with vascular grafting prosthesis fabric are also available for endovascular application, to repair damaged blood vessels may also be coated. Coating or incorporating the compositions of the present invention into such medical devices can inhibit infection, where the presence of infection can have significant deleterious effects on the patient, often necessitating removal and replacement.

Suture material can also harbor infections. Sutures are commonly made of prolene, nylon or other mono-filamentous non-absorbable materials, and absorbable materials such as catgut and polyglycolic acid. Suture materials comprising a composition of the present invention would have increased resistance to infection, thereby increasing their efficacy and the recovery of a patient. Fabricating an absorbable or a nonabsorbable suture comprising a composition of the invention and which retains the handling and tensile characteristics of the material is within the skill of artisans in the field.

When a foreign object becomes infected after surgery, it most likely needs to be removed so that the infection can be controlled. Wound infections can penetrate to deeper levels of the tissues to involve foreign material that has been used as part of the operation. As an example, hernias are commonly repaired by suturing a plastic screening material called mesh in the defect. Surgical meshes comprising a composition of the invention can have increased resistance to infection. Surgical meshes are made of substances like e-PTFE, poly(tetrafluoroethylene), nylon, crystalline poly (propylene) and high-density poly(ethylene). Avoiding infection of these materials is of great importance, because of infection can be life threatening. Materials used for meshes and related materials can be formulated to be coated with or have incorporated into the claimed compositions of the instant invention.

Certain implantable devices intended to restore structural stability to body parts can be advantageously treated and/or coated with the instant claimed compositions. For example, implantable devices, used to replace bones or joints or teeth, act as prostheses or substitutes for the normal structure present at that anatomic site. Metallics and ceramics are commonly used for orthopedic and dental prostheses. Implant may be anchored in place with cements like polymethylmethacrylate. Prosthetic joint surfaces can be fabricated from polymers such as silicones or poly(tetrafluoroethylene). Entire prosthetic joints for fingers, toes or wrists can be made from polymers.

Implantable devices for cosmetic or reconstructive applications may employ the present invention to inhibit biofilm formation. Examples include breast implants and tissue expanders. These devices may be made of silicone elastomers or other naturally occurring or synthetic biomaterials. In contrast to permanent implants, such as breast implants, a tissue expander is usually intended for temporary use; once the overlying tissues are adequately expanded, they are stretched to cover their intended defect. If an expander needs to be removed as the result of infection and/or subsequent biofilm formation, the tissue will return to its normal state. Use of a composition of the present invention may reduce the incidence of bacterial contamination, biofilm development and subsequent local infection.

Insertable devices include those objects made from synthetic materials applied to the body or partially inserted into the body, through a natural or an artificial site of entry. A non-exhaustive list of articles applied to the body include contact lenses, stoma appliances, an artificial larynx, endotracheal or tracheal tubes, catheters (peritoneal, urinary, etc.), biliary drainage tubes, gastronomy tubes and maxillofacial prostheses. These devices are made of a variety of materials including plastics and polymers. The formation of biofilm on any of these devices permits the ingress of microorganisms along the device from a more external anatomic area to a more internal anatomic area. This can cause local and systemic infections that can have significant impact on the health of a patient. The present invention may be incorporated onto as a coating or into as a comonomer the device to reduce contamination by biofilm formation on the surface of the device.

Materials applied to the body can advantageously employ the compositions disclosed herein. Dressing materials can themselves incorporate or be coated with the compositions, as in a film or sheet to be applied directly to a skin surface. Additionally, the biofilm resistant compositions of the instant invention can be incorporated in the glue or adhesive used to adhere the dressing materials or appliance to the skin. Stoma adhesive or medical-grade glue may, for example, be formulated to include a composition of the present invention appropriate to the particular medical setting. Other affixation devices can be similarly treated. Bandages, adhesive tapes and clear plastic adherent sheets are further examples where the incorporation or coating with a biofilm resistant composition in the glue or other adhesive used to affix the object, or incorporation as a component of the object itself, may be beneficial in reducing skin irritation and infection.

These above examples are offered to illustrate the multiplicity of applications of compositions of the invention in medical devices. Other examples will be readily envisioned by skilled artisans in these fields. The scope of the present invention is intended to encompass all those surfaces and materials where the presence of fouling has adverse health-related consequences. The examples given above represent embodiments where the technologies of the present invention are understood to be applicable. Other embodiments will be apparent to practitioners of these and related arts. Embodiments of the present invention can be compatible for combination with currently employed antiseptic regimens to enhance their antimicrobial efficacy or cost-effective use. Other examples of applications in medical environments to promote antisepsis will be readily envisioned by those of ordinary skill in the relevant arts.

The present invention is further illustrated by the following examples, which should not be construed as limiting in any way. The contents of all cited references including literature references, issued patents and published patent applications as cited throughout this patent application are hereby expressly incorporated by reference.

EXAMPLES

Example 1

Materials and Laboratory Synthesis of the Monomers of the Present Invention

The well plates and most chemicals used in the monomer syntheses and testing, including the alcoholic precursors, triethylamine (TEA), acryloyl chloride, well plates, and acetonitrile, were purchased from Sigma-Aldrich. The dichloromethane also used in the syntheses was purchased from Pharmacia. The material used for the coating formulations was obtained from Allied Photochemical and is a proprietary formulation. Cytec Specialty Chemicals provided HDODA used in the photo-DSC testing. Albemarle Corporation donated the initiator, 2,2-dimethoxy-2-acetophenone (DMPA) used in the photo-DSC studies. The uncoated, polished stainless steel plates were purchased from Q-Panel Products. Methyl ethyl ketone (MEK) for the double rub solvent resistance test was purchased from The Paint Center. Pap-smear cytology fixative spray was obtained from Andwin Scientific. The E. coli was stained using Hema-diff solution 3:thiazine dye from Anapth.

Each alcohol precursor was dissolved in dichloromethane after adding TEA in slight molar excess. Under a ventilation hood, acryloyl chloride was added dropwise producing hydrogen chloride gas, which was, inpart, consumed by the TEA. The round bottom flask was purged with nitrogen for five seconds and stoppered to provide a nitrogen atmosphere for the reaction to take place. The reaction mixture stirred for 24 hours at room temperature using a magnetic stir bar to allow for complete reaction. TEA.HCl precipitate formed which was removed by suction filtration. Unreacted acryloyl chloride was removed by washing with five milliliters (5 ml) of deionized water five times in a separatory funnel. A rotary evaporator was used to remove any excess dichloromethane. The reaction scheme is shown below (Reaction 1).

Reaction 1: Laboratory Scale Monomer Synthesis

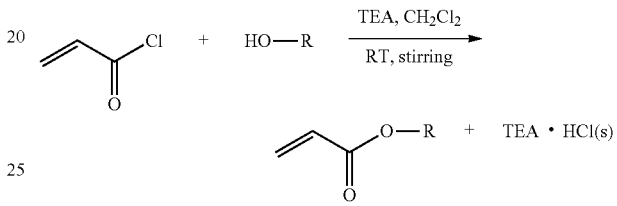

The structure of each monomer was verified by infrared spectroscopy (IR) and nuclear magnetic resonance (NMR).

Furthermore, it is recognized that the industrial synthesis would involve a synthetic scheme involving either: 1) the esterification reaction of acrylic acid with the alcoholic precursor, or 2) the transesterification reaction of methyl acrylate (or similar derivative) with the alcoholic precursor with both procedures requiring an acid catalyst, elevated temperatures, and a vacuum to remove the condensate from the reaction vessel.

Example 2

Polymerization Rates of the Compositions by Photo-Differential Scanning Calorimetry (Photo-DSC)

To determine the relative polymerization rate of the preferred compositions of the present invention, photo-DSC was performed on UV-curable formulations containing each of the five monomers [i.e., phenyl acrylate (PA), 3-chlorophenyl acrylate (CPA), 2,4-dichlorophenyl acrylate (DCPA), 4-bromophenyl acrylate (BPA) and 2,4-dibromophenyl acrylate (DBPA)], as described in Example 1.

For the photo-DSC runs, two microliters (2 µL) of each formulation was measured into crimped, aluminum sample pans. After placing under the quartz window of the photo-DSC head, the light intensities were measured using black body absorbers and were approximately 30 mW/cm$^2$. The calorimetric measurements were performed using a Mettler-Toledo DSC 822$^e$ modified with a Hamamatsu Lightning Cure 200 UV-spot, equipped with a high pressure mercury vapor lamp. The sample cell was kept at a constant 20° C. by a Julabo FT 100 intercooler. The polymerization rates of each monomer were compared to that of a standard Type I initiated sample and to that of HDODA at 100 weight percent.

The monomers were mixed in similar percentages (5, 10, 15, and 20 weight percent) as done with the biological assessment into 1,6-hexanediol diacrylate (HDODA) and evaluated for their activity as photoinitiating species. As standards, HDODA (100 weight percent) and a mixture of HDODA and DMPA (99.0 and 1.0 weight percent, respectively) were also run. In each case, the active monomer did not function as a photoinitiating species as observed from the relatively low exotherm, which was comparable to that of the HDODA at 100 weight percent and much reduced compared to that of the DMPA initiated mixture. The photo-DSC study also demonstrates that the monomers are relatively photolytically stable given that they did not dissociate to form initiating species.

Example 3

Physical Characteristics and Testing of the Composition

The coatings were formulated having five, ten, fifteen, and twenty weight percent of the potentially biofilm resistant monomers. A two mil (50 μm) thick coating was applied with a metal draw-down bar. The coatings were cured by a custom designed apparatus to provide a nitrogen atmosphere (2 minute purging prior to cure and continued purging during cure). This allowed UV radiation exposure (5 minutes) using a Sylvania medium pressure mercury arc lamp (HPL80MDX(R) 80 Watt (RQ) 0303) source which the outer casing had been removed. The intensity was 15 mW/cm$^2$ at the top of the lid after a thirty (30) minute warm up period. The metal plate was enclosed in a screwed down lid (13"×9" Pyrex casserole dish) with nitrogen running through it to provide an oxygen-free, nitrogen atmosphere. Determination of complete curing was based on a basic thumb twist test, as is known in the art.

These coatings were applied to stainless steel plates. To determine the physical characteristics and attributes of the polymers created in Example 1, the pencil hardness (ASTM D3363), MEK double rub (ASTM D5402-93), and cross hatch adhesion (ASTM D 3359) tests were performed (as given in standard source).

The pencil hardness test showed adding the monomer to the coating increased the hardness as the concentration of the monomer increased. This is caused by the additional physical crosslinking due to increased dipole-dipole interactions from the higher concentration of monomer.

The MEK double rub solvent resistance test showed the association between monomer physical and chemical crosslinking with the solvent resistance. The solvent resistance generally increased when low concentrations of the monomer were added. The low concentration of the monofunctional monomer does not greatly decrease the chemical crosslinking while increasing physical crosslinking thereby leading to a higher chemical resistance. Since the monofunctional monomer is highly polar, the molecular interactions (physical crosslinks) are increased in the polymer resulting in an increased solvent resistance. When the concentration of the monomer increased, the degree of chemical crosslinking decreased lowering the solvent resistant properties of the coating.

In the cross hatch adhesion test, the adhesive forces between the metal plate and the coating was not affected when the monomer was added. This shows consistent adhesive properties at varying monomer concentrations.

Example 4

Biofilm Resistance of the Compositions

In order to determine whether the above-described compounds were biofilm resistant, four novel, biofilm resistant monomers and a non-biofilm resistant control monomer were synthesized and formulated into a commercially available ultraviolet (UV) curable coating for metals at varying weight percents. Materials and methods were the same as disclosed in the Examples 1 and 2, above, except that the polymers were not adhered to steel, but to 24-well, plastic (i.e., poly(styrene)) culture plates.

The coatings were applied to and UV-cured onto four uncoated 24-well plastic plates to a calculated thickness of two mils. The monomers of the compositions were phenyl acrylate (PA) as the non-biofilm resistant control monomer, 3-chlorophenyl acrylate (CPA), 2,4-dichlorophenyl acrylate (DCPA), 4-bromophenyl acrylate (BPA) and 2,4-dibromophenyl acrylate (DBPA).

The coatings were cured with the curing apparatus and sterilized with 95% ethanol. E. coli was grown in a LB agar broth and added to the cell plates with sterile, deionized water at four concentrations, one concentration per plate. The plates were incubated for twenty-four hours at 37° C. The E. coli was then rinsed from the plates with sterile, deionized water and sprayed with the cytology fixative [poly(ethylene glycol)-based]. After the fixative was air dried it was soaked with 95% ethanol for ten minutes for further sterilization. The plates were then rinsed with sterile, deionized water and four drops of Hema-diff solution were added for four seconds. After the dye was removed, the plates were rinsed with sterile, deionized water showing residual dyed bacteria on the coating (i.e., the presence of a biofilm).

The outcome of the biological testing showed bacterial growth, evidenced by the blue tinting, on the coatings containing the internal control, PA, and the unmodified control formulation with no added PA or halogenated phenyl acrylate derivatives (FIG. 4).

The coatings containing the lowest concentrations of biofilm resistant monomer (5 weight %) had small amounts of bacterial growth (FIG. 4). However, when the concentration of these same monomers increased, the biofilm resistance of the coatings increased. The two highest concentrations (15 and 20 weight %) of CPA, DCPA, and DBPA had excellent biofilm resistance given the lack of blue coloring (FIG. 4). As expected, when the concentration of E. coli broth increased (approaching 10$^9$ cells/mL) among differing plates, the bacterial growth increased though no evidence of biofilm formation was observed on the 15 and 20 weight percent CPA, DCPA, or DBPA (FIG. 4). The surface of the coating was very rough as it was spread across the bottom of the well by a toothpick; thus, the biofilm resistance is postulated to be primarily due to unfavorable surface chemistry for bacterial accumulation caused by the addition of the very polar monomers to the formulation. It is further postulated that the surface polarity of the coatings was somewhat negative thereby inhibiting bacterial attachment through the phosphate groups comprising, in part, the lipid bilayer of the bacterial cell walls.

Example 5

Roughness Quantization of the Compounds

To determine the roughness of the cured formulations, polymers consisting of each of five monomers were tested using atomic force microscopy (AFM) scanning and applying the non-contact mode dragging of the cantilever. Each of the polymers consisting of the monomers: phenyl acrylate (PA), 3-chlorophenyl acrylate (CPA), 2,4-dichlorophenyl acrylate (DCPA), 4-bromophenyl acrylate (BPA) and 2,4- dibromophenyl acrylate (DBPA) were tested at 5, 10, 15 and 20 percent of the monomer by weight (the "Coating Level"). Method of preparing the polymer compositions is described above in Examples 1 and 3.

Each scanning location was approximately an 80 μm×80 μm area (6400 μm²). To eliminate the effects of interference on the roughness measurements, two scans were taken at each location in the X and Y direction. These two roughness calculations were averaged to yield the roughness calculation for each location. Three locations were selected for each plate and then the average roughness was calculated for all three locations in order to minimize statistical variance yielding an overall plate roughness average, $S_a$ as determined via Equation 1.

$$S_a = \frac{1}{MN} \sum_{k=0}^{M-1} \sum_{l=0}^{N-1} |z(x_k, y_l)| \quad \text{Equation 1}$$

Figure 2:
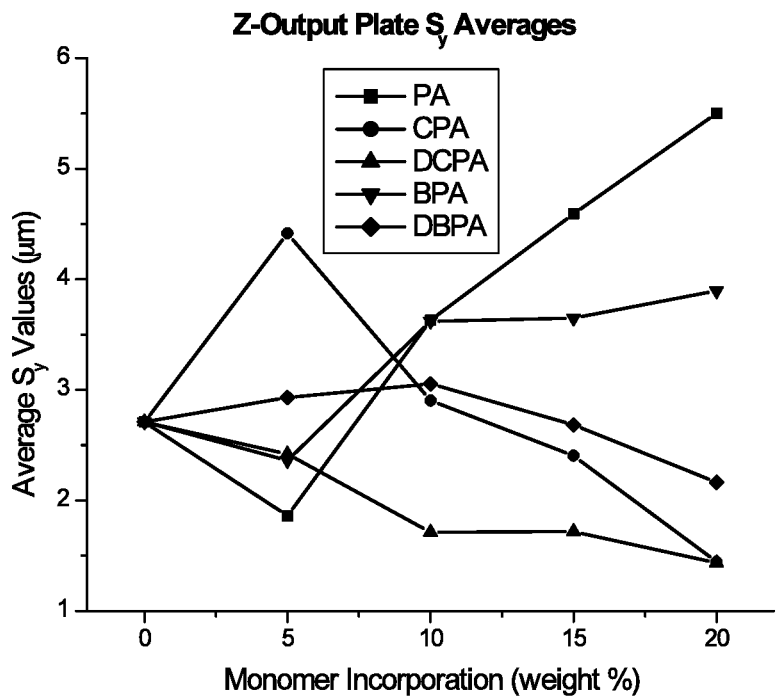
FIG. 2 is a graphical illustration of measurements of the average roughness of exemplary compositions as a value of $S_y$ (the peak to valley distance) in micrometers (μm). The Z-Output Plate is representative of an alternative accepted method of measuring roughness, as is well known in the art. Each composition was plated at a coating level of 20, 15, 10 and 5 weight percent of the monomer tested. The compositions tested are labeled as their monomer components: 4-bromophenyl acrylate (BPA), 3-chlorophenyl acrylate (CPA), 2,4-dibromophenyl acrylate (DBPA), 2,4-dkhlorophenyl acrylate (DCPA), and phenyl acrylate (PA).
Figure 2:
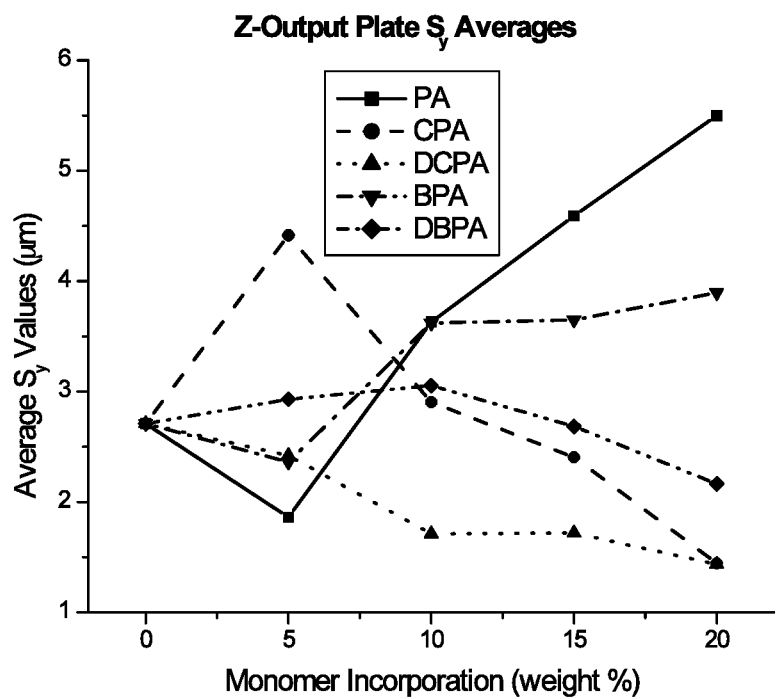
Figure 3:
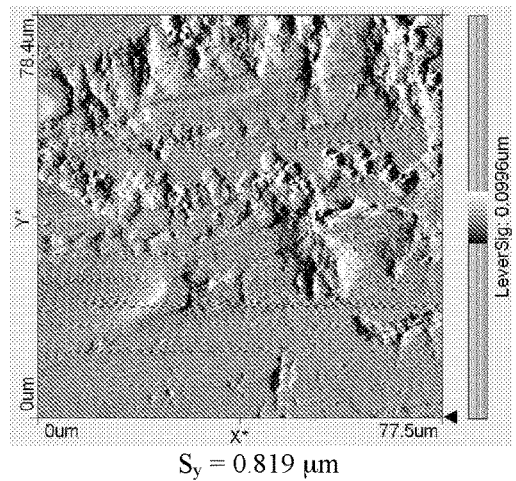
FIG. 3 is a depiction of the composition illustrating its smoothness relative to that of uncoated, cold-rolled steel. For comparison, electropolished, surgical grade steel has an average peak to valley height ($S_y$) of 1.0 mm which can be compared to the $S_y$ values given for each sample.
Figure 3:
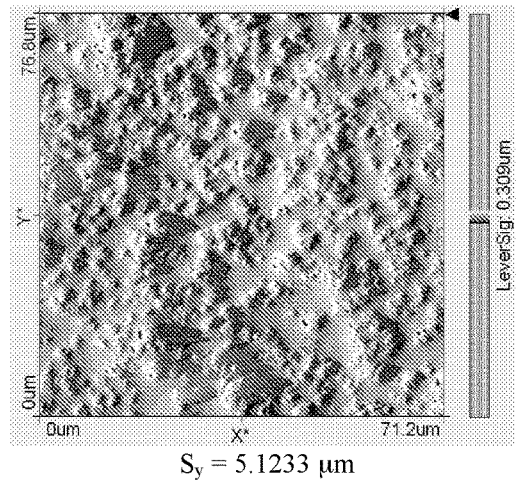
Figure 3:
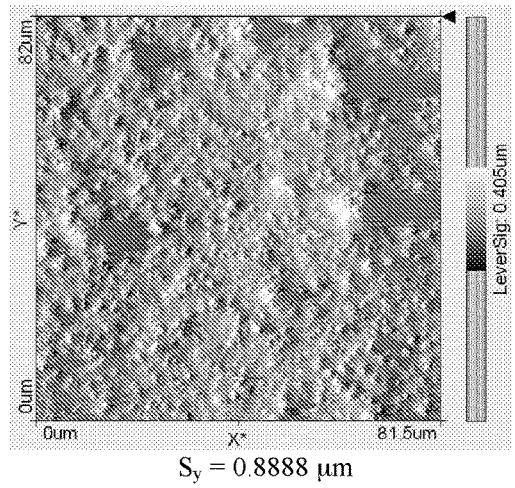
Figure 3:
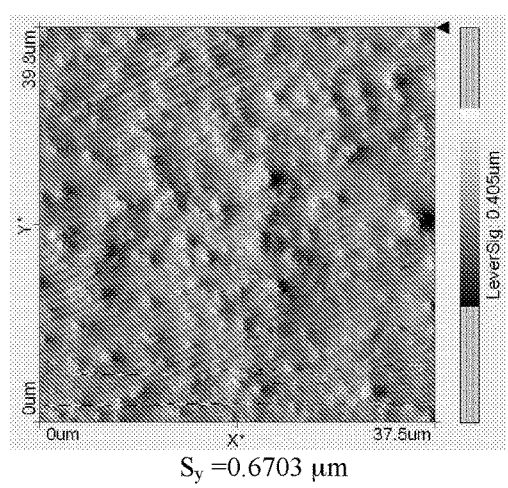

Graphs depicting the collected data were prepared using the average roughness values ($S_a$) for each of the plates as well as the average peak to valley distance, $S_y$, values for each of the plates as depicted in FIGS. 1 and 2. The following equation was used to determine the average peak to valley distance, $S_y$ value, (Equation 2) for each composition at each coating level.

$$S_y = S_{peak} - S_{valley} \quad \text{Equation 2}$$

The $S_y$ value is the value typically used in the industry to determine the propensity for biofilm resistance of a smooth surface.

Data collected from this testing demonstrates that the polymers incorporating the biofilm resistant monomer have a $S_y$ value that begins to approximates that of electropolished stainless steel (i.e., surgical grade steel), which has a $S_y$ value of 1.0 mm. (FIGS. 1 and 2) Therefore, the biofilm resistant monomers seem to act as flow and leveling agents for the coatings thereby enhancing the smoothness of the coating. The addition of PA, the non-biofilm resistant control monomer, did not enhance the smoothness; this may contribute, in part, to the inactivity of PA as a biofilm resistant agent.

Those skilled in the art will recognize, or be able to ascertain using no more than routine experimentation, many equivalents of the specific embodiments of the invention described herein. Such equivalents are intended to be encompassed by the following claims.

The invention claimed is:

1. A method of rendering a thermoplastic polymer resistant to biofilm formation comprising:
    incorporating said thermoplastic polymer with a curable composition comprising:
        a mixture of an alkene-based formulation sufficient to adhere to said substrate surface when polymerized;
        a polymerizable halogenated aryl compound of structure A:

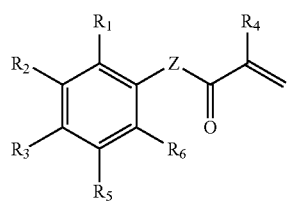

wherein $R_1$, $R_2$, $R_3$, $R_5$, or $R_6$ represents Chlorine, Bromine, Hydrogen, or an organic moiety selected from the group consisting of alkyl, aryl, alcoholic, etheric, thioesteric, esteric, amido, amino, thiol, urethane, and acid anhydride, wherein $R_4$ is a hydrogen, methyl group, or methacrylate, wherein at least one of $R_1$, $R_2$, $R_3$, $R_5$, or $R_6$ is Chlorine or Bromine; and wherein Z represents Oxygen; and
    providing an energy source sufficient to polymerize said polymerizable halogenated aryl compound;
    polymerizing the curable composition into said thermoplastic polymer, such that the curable composition renders the surface of said thermoplastic or thermoset polymer resistant to biofilm formation and having a roughness that approximates electropolished stainless steel.

2. The method of claim 1, wherein said polymerizable halogenated aryl compound is 2, 4-dibromophenyl acrylate, having Structure B:

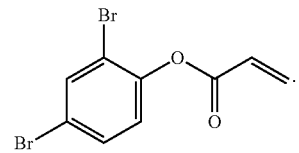

3. The method of claim 1, wherein the energy source is ultraviolet, visible, infrared, or microwave radiation.

4. The method of claim 1, wherein polymerization of said polymerizable halogenated aryl compound takes place in the presence of an alkene-based monomer.

5. The method of claim 1, wherein the polymerizable halogenated aryl compound is between approximately 0.5% and 35% of the polymer by weight.

6. The method of claim 1, wherein the polymerizable halogenated aryl compound may be either mono- or multifunctional in the number of polymerizable groups, selected from the group consisting of acrylates, methacrylates, thiols and alkenes, to which said polymerizable halogenated aryl compound is covalently bound.

7. A method of rendering a thermoplastic polymer resistant to biofilm formation comprising:
    incorporating said thermoplastic polymer into curable composition comprising of a biofilm resistant monomer of structure A:

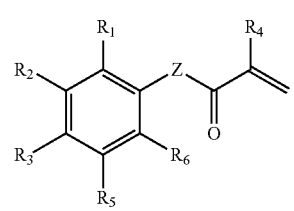

wherein $R_1$, $R_2$, $R_3$, $R_5$, or $R_6$ represents Chlorine, Bromine, Hydrogen, or an organic moiety selected from the group consisting of alkyl, aryl, alcoholic, etheric, thioesteric, esteric, amido, amino, thiol, urethane, and acid anhydride, wherein $R_4$ is a hydrogen, methyl group, or methacrylate, wherein at least one of $R_1$, $R_2$, $R_3$, $R_5$, or $R_6$ is Chlorine or Bromine; and wherein Z represents Oxygen; and curing said curable composition and biofilm resistant monomer into said thermoplastic and rendering the surface of said thermoplastic polymer resistant to biofilm formation and having a smoothness that approximates electropolished stainless steel.

8. The method of claim 7, wherein said polymerizable halogenated aryl compound is 2, 4-dibromophenyl acrylate, having Structure B:

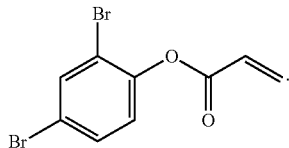

9. The method of claim 7, wherein said monomer may be mono- or multi-functional in the number of polymerizable groups, selected from the group consisting of acrylates, methacrylates, thiols and alkenes, to which the monomer is covalently bound.

10. The method of claim 7, wherein the energy source is ultraviolet, visible, infrared, or microwave radiation.

11. The method of claim 7, wherein polymerization of said monomer takes place in the presence of 1,6-hexandiol diacrylate.

12. The method of claim 7, wherein the monomer is between approximately 0.5% and 35% of the polymer by weight.

13. The method of claim 7, wherein polymerization of said monomer into said thermoplastic or thermoset polymer renders said thermoplastic or thermoset polymer with a smoothness wherein the peak to valley ratio of the surface has a value of approximately 1 μm.

14. The method of rendering a thermoplastic polymer resistant to biofilm formation of claim 1, wherein the polymerizable halogenated aryl compound has structure A:

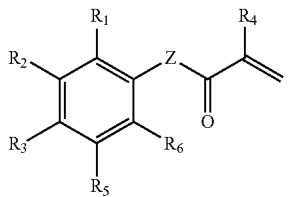

wherein $R_1$, $R_2$, $R_3$, $R_5$, or $R_6$ represents Chlorine, Bromine, Hydrogen, or an organic moiety selected from the group consisting of alkyl, aryl, alcoholic, etheric, thioesteric, esteric, amido, amino, thiol, urethane, and acid anhydride, wherein $R_4$ is a hydrogen, methyl group, or methacrylate, wherein at least one of $R_1$, $R_2$, $R_3$, $R_5$, or $R_6$ is Chlorine or Bromine; and wherein Z represents Oxygen; and polymerizing the polymerizable halogenated aryl compound, wherein the polymerizable halogenated aryl compound does not leach into a surrounding environment and is not biocidal, the polymerizable halogenated aryl compound serving as a biofilm remediation agent, reducing the amount of biologics that can attach and colonize on the polymer and does not need to be acrylic or methacrylic in nature.

15. A method of rendering a thermoplastic polymer resistant to biofilm formation comprising:

a curable composition comprising of a biofilm resistant monomer of structure A:

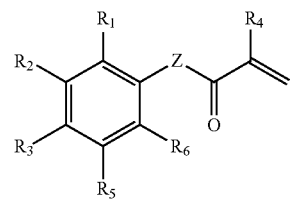

wherein $R_1$, $R_2$, $R_3$, $R_5$, or $R_6$ represents Chlorine, Bromine, Hydrogen, or an organic moiety selected from the group consisting of alkyl, aryl, alcoholic, etheric, thioesteric, esteric, amido, amino, thiol, urethane, and acid anhydride, wherein $R_4$ is a hydrogen, methyl group, or methacrylate, wherein at least one of $R_1$, $R_2$, $R_3$, $R_5$, or $R_6$ is Chlorine or Bromine; and wherein Z represents Oxygen; and curing said curable composition produces said thermoplastic polymer whose surface is biofilm resistant and as a roughness that approximates electropolished stainless steel.

* * * * *